United States Patent
Koyrakh et al.

(10) Patent No.: US 9,585,586 B2
(45) Date of Patent: Mar. 7, 2017

(54) NAVIGATIONAL REFERENCE DISLODGEMENT DETECTION METHOD AND SYSTEM

(75) Inventors: Lev A. Koyrakh, Plymouth, MN (US); Jeffrey A. Schweitzer, St. Paul, MN (US); Daniel R. Starks, Lake Elmo, MN (US); Carlos Carbonera, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1746 days.

(21) Appl. No.: 12/972,253

(22) Filed: Dec. 17, 2010

(65) Prior Publication Data

US 2012/0157825 A1    Jun. 21, 2012

(51) Int. Cl.
*A61B 5/042* (2006.01)
*A61B 5/00* (2006.01)

(52) U.S. Cl.
CPC ............ *A61B 5/042* (2013.01); *A61B 5/7221* (2013.01)

(58) Field of Classification Search
CPC ...................................... A61B 5/042
USPC ........................ 600/407, 424, 435
See application file for complete search history.

(56) References Cited

U.S. PATENT DOCUMENTS

| | | | |
|---|---|---|---|
| 5,263,493 A | 11/1993 | Avitall |
| 5,280,429 A | 1/1994 | Withers |
| 5,335,668 A | 8/1994 | Nardella |
| 5,391,199 A | 2/1995 | Ben-Haim |
| 5,487,385 A | 1/1996 | Avitall |
| 5,500,011 A | 3/1996 | Desai |
| 5,568,809 A | 10/1996 | Ben-Haim |
| 5,694,945 A | 12/1997 | Ben-Haim |
| 5,697,377 A | 12/1997 | Wittkampf |

(Continued)

FOREIGN PATENT DOCUMENTS

| | | |
|---|---|---|
| EP | 2204121 | 7/2010 |
| WO | 2004/107978 | 12/2004 |
| WO | 2008/083111 | 7/2008 |

OTHER PUBLICATIONS

International Search Report for PCT/US07/88675 filed Dec. 21, 2007, with Written Opinion of the International Searching Authority dated May 1, 2008.

(Continued)

*Primary Examiner* — Rochelle Turchen
(74) *Attorney, Agent, or Firm* — Wiley Rein LLP

(57) ABSTRACT

A method of detecting dislodgement of a navigational reference for a localization system includes securing a reference catheter, including at least one reference localization element, at an initial reference location within a localization field. The positions of one or more of the reference localization elements are monitored for a perceived displacement that suggests that the reference catheter has become dislodged from the initial reference location (e.g., a displacement above a certain threshold, such as about 4 mm). The direction of this perceived displacement may then be further analyzed (e.g., compared to a predicted or most likely direction of displacement) to determine whether there has been an actual dislodgement of the reference catheter, and, if so, an appropriate signal (e.g., an audible or visual warning) may be generated. Upon dislodgement, guidance may be provided to aid the practitioner in restoring the reference catheter to its initial location.

18 Claims, 5 Drawing Sheets

(56) References Cited

U.S. PATENT DOCUMENTS

| | | |
|---|---|---|
| 5,732,710 A | 3/1998 | Rabinovich et al. |
| 5,840,025 A | 11/1998 | Ben-Haim |
| 5,842,984 A | 12/1998 | Avitall |
| 5,954,665 A | 9/1999 | Ben-Haim |
| 5,983,126 A | 11/1999 | Wittkampf |
| 6,115,626 A | 9/2000 | Whayne et al. |
| 6,129,669 A | 10/2000 | Panescu et al. |
| 6,226,542 B1 | 5/2001 | Reisfeld |
| 6,233,477 B1 | 5/2001 | Chia et al. |
| 6,332,089 B1 | 12/2001 | Acker et al. |
| 6,640,119 B1 | 10/2003 | Budd et al. |
| 6,728,562 B1 | 4/2004 | Budd et al. |
| 6,858,003 B2 | 2/2005 | Evans et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 2002/0169378 A1* | 11/2002 | Mo et al. ............ 600/437 |
| 2004/0254437 A1 | 12/2004 | Hauck et al. |
| 2005/0119639 A1 | 6/2005 | McCombs et al. |
| 2005/0203382 A1 | 9/2005 | Govari et al. |
| 2005/0222554 A1 | 10/2005 | Wallace et al. |
| 2006/0084863 A1 | 4/2006 | Kluzik et al. |
| 2006/0095022 A1 | 5/2006 | Moll et al. |
| 2006/0100610 A1 | 5/2006 | Wallace et al. |
| 2007/0060833 A1 | 3/2007 | Hauck |
| 2007/0185486 A1 | 8/2007 | Hauck |
| 2008/0009758 A1 | 1/2008 | Voth |
| 2008/0161681 A1 | 7/2008 | Hauck |
| 2009/0030307 A1 | 1/2009 | Govari et al. |
| 2010/0152801 A1 | 6/2010 | Koh et al. |
| 2010/0305429 A1 | 12/2010 | Shachar et al. |

OTHER PUBLICATIONS

International Search Report and Written Opinion for PCT/US11/51441, dated Jan. 5, 2012.

Wittkampf et al.: "LocalLisa: New technique for real-time 3-dimensional localization of regular intracardiac electrodes" Cirulation, vol. 99, No. 10, Mar. 16, 1999, pp. 1312-1317.

Supplementary European Search Report issued in EP Patent Application No. 11848900.4 (Apr. 8, 2014).

* cited by examiner

NAVIGATIONAL REFERENCE DISLODGEMENT DETECTION METHOD AND SYSTEM

CROSS-REFERENCE TO RELATED APPLICATIONS

This application is related to U.S. application Ser. No. 11/647,277, filed 29 Dec. 2006, which is hereby incorporated by reference as though fully set forth herein.

BACKGROUND OF THE INVENTION a. Field of the Invention

The instant invention relates generally to the navigation of a medical device through a patient. More specifically, the instant invention relates to a method and system for detecting the movement of a reference point utilized in a non-ionizing localization system, such as is often employed in navigating a medical device through a patient, and mitigating the effects of such reference point movement.

b. Background Art

It is well known to generate heart chamber geometry in preparation for cardiac diagnostic or therapeutic procedures. Often, a mapping catheter tip is placed within the heart chamber and/or against the wall of the heart chamber and the three-dimensional coordinates of the mapping catheter tip are measured using a localization system. The three-dimensional coordinates become a geometry point. Multiple measurements are taken as the mapping catheter is moved within the heart chamber, resulting in a cloud of geometry points (also referred to as "location data points") that defines the geometry of the heart chamber. Various surface construction algorithms may then be applied to wrap a surface around the cloud of geometry points to obtain a three-dimensional representation of the heart chamber geometry.

It is desirable for the three-dimensional coordinate system relative to which the geometry points are measured to have a stable reference point or origin. This stable reference point or origin is referred to herein as a "navigational reference" for the localization system. While any stable position will suffice, it is desirable for many reasons to utilize a navigational reference that is proximate to the mapping catheter. Thus, a catheter-mounted reference localization element is often inserted into the heart and positioned in a fixed location, such as the coronary sinus, to establish the origin of the coordinate system relative to which the location of the mapping catheter will be measured.

It is known, however, that the navigational reference may become dislodged. For example, the mapping catheter may collide or become entangled with the catheter carrying the navigational reference (referred to herein as the "reference catheter"), or the practitioner moving the mapping catheter may inadvertently jostle the reference catheter. The navigational reference may also be dislodged by patient movement. Other factors, such as patient hydration and respiration, may make it appear as if the navigational reference has become dislodged when, in fact, it has not become dislodged.

When the navigational reference becomes dislodged, it effectively shifts the origin of the coordinate system used by the localization system. Unless the dislodgement is detected and accounted for, positions of the mapping catheter measured after the dislodgement will be invalid.

BRIEF SUMMARY OF THE INVENTION

It is therefore desirable to be able to detect dislodgement of the navigational reference that defines the origin of the coordinate system relative to which body geometries are measured.

Additionally, it is desirable to be able to distinguish mechanical dislodgement of a navigational reference from "false" dislodgements of the navigational reference.

It is also desirable to guide a user in reestablishing the original position of the navigational reference.

It is further desirable to provide a method by which the original position of the navigational reference may be reestablished.

In addition, it is desirable to provide a method that accounts for the dislodged location of the navigational reference without requiring reestablishment of the original position of the navigational reference.

According to a first aspect of the invention, a method of detecting dislodgement of a navigational reference within a localization field includes the following steps: placing a reference catheter including at least one reference localization element within a localization field; securing the reference catheter at an initial reference location within the localization field; computing a slow-moving average location of the at least one reference localization element; computing a fast-moving average location of the at least one reference localization element; computing a distance between the slow- and fast-moving average locations of the at least one reference localization element; comparing the computed distance to a dislodgement threshold; determining that a dislodgement of the reference catheter from the initial reference location has occurred; and generating a signal indicative of the dislodgement of the reference catheter from the initial reference location. A suitable dislodgement threshold is about 4 mm.

As a further check to determine whether the dislodgement is actual or merely perceived, the method may include the following optional steps for the at least one reference localization element if the computed distance exceeds the dislodgement threshold: computing a vector connecting the slow- and fast-moving average locations of the respective reference localization element at a point in time when the computed distance between the slow- and fast-moving average locations of the respective reference localization element exceeded the dislodgement threshold; determining an axis of the reference catheter proximate the respective reference localization element at the point in time when the computed distance between the slow- and fast-moving average locations of the respective reference localization element exceeded the dislodgement threshold; and computing an angle between the computed vector and the axis of the reference catheter proximate the respective reference localization element, thereby computing at least one angle associated with the at least one reference localization element; and analyzing the at least one angle for an indication that the reference catheter has dislodged from the initial reference location. The step of analyzing the at least one angle for an indication that the reference catheter has dislodged from the initial reference location may include: determining a count of angles exceeding a sharp angle threshold; and comparing the count of angles to a count threshold.

Likewise, the axis of the reference catheter proximate each reference localization element may be defined in any suitable fashion. For example, the axis of the reference catheter proximate the respective reference localization element may be defined by a line segment connecting the respective reference localization element to a neighboring reference localization element.

In some embodiments of the invention, the fast-moving average location of the at least one reference localization element is computed with a filter time constant of about 12 seconds. Suitable filters for computing the slow- and/or fast-moving average locations include: exponential moving average filters, moving average filters, infinite impulse response filters, finite impulse response filters, and any combinations thereof.

In the event that the reference catheter becomes dislodged, the method optionally includes providing guidance to a user to help re-position and secure the reference catheter proximate the initial reference location. As an alternative to re-positioning the reference catheter proximate the initial reference location, the method may include: defining a new stable location of the reference catheter; calculating a reference adjustment to compensate for any change in position of the reference catheter between the initial reference location and the new stable location; and using the reference adjustment to adjust localization element position measurements made after the dislodgement from the initial reference location.

In another aspect of the invention, a method of detecting dislodgement of a navigational reference within a non-ionizing localization field includes: securing a reference catheter including a plurality of reference localization elements at an initial reference location within the localization field; detecting a perceived displacement of the reference catheter from the initial reference location; analyzing a direction of the perceived displacement to determine whether there has been a dislodgement of the reference catheter from the initial reference location; and generating a signal indicating a dislodgement of the reference catheter from the initial reference location. The method optionally includes the steps of: calculating a reference adjustment to compensate for any change in position of the reference catheter after the dislodgement from the initial reference location; and using the reference adjustment to adjust localization element position measurements made after the dislodgement from the initial reference location. Alternatively, the method may include providing guidance to a user to help re-position and secure the reference catheter proximate the initial reference location.

In some embodiments of the invention, the detecting step involves comparing a magnitude of a perceived displacement of at least some of the plurality of reference localization elements to a dislodgement threshold. Likewise, the analyzing step may involve comparing a direction of a perceived displacement of at least some of the plurality of reference localization elements to an anticipated dislodgement direction.

Also disclosed herein is a localization system that includes: a plurality of localization field generators; a reference catheter including a plurality of reference localization elements; and a reference catheter dislodgement processor that monitors for a dislodgement of the reference catheter from an initial reference location based, at least in part, on a difference between a slow-moving average location and a fast-moving average location of at least some of the plurality of reference localization elements on the reference catheter. It is also contemplated that the dislodgement processor may monitor for a dislodgement of the reference catheter from its initial reference location based, at least in part, on a correlation between a perceived direction of dislodgement (e.g., a vector connecting the slow- and fast-moving average locations) and a predicted direction of dislodgement (e.g., a vector along the reference catheter axis).

In some embodiments of the invention, the reference catheter dislodgement processor: compares the difference between the slow-moving average location and the fast-moving average location of at least some of the plurality of reference localization elements to a dislodgement threshold, and, if the difference exceeds the dislodgement threshold: computes, for at least some of the plurality of reference localization elements, an angle between a vector connecting the slow- and fast-moving average locations of the reference localization element and an axis of the reference catheter proximate the reference localization element, thereby computing a plurality of angles; determines a count of angles exceeding a sharp angle threshold; and compares the count of angles to a count threshold to determine whether the reference catheter has dislodged from the initial reference location. The reference adjustment processor may also: calculate a reference adjustment to compensate for any change in position of the reference catheter after the dislodgement from the initial reference location; and use the reference adjustment to adjust localization element position measurements made after the dislodgement from the initial reference location.

An advantage of the present invention is that it may be used to alert a user to dislodgement of the navigational reference.

A further advantage of the present invention is that it may guide the user in mitigating the dislodgement.

Another advantage of the present invention is that it can automatically correct for the dislodgement, for example by calculating a reference adjustment to compensate for the changed position of the navigational reference.

Still another advantage of the present invention is that it distinguishes between actual mechanical dislodgements of the navigational reference and "false" dislodgements thereof.

The foregoing and other aspects, features, details, utilities, and advantages of the present invention will be apparent from reading the following description and claims, and from reviewing the accompanying drawings.

DETAILED DESCRIPTION OF THE INVENTION

The present invention, which is preferably practiced in connection with a localization system, automatically detects dislodgement of a navigational reference for the localization system. In addition, the present invention provides methods of automatically correcting for the dislodgement or to guide a user, e.g., a physician, in repositioning the navigational reference at its original location.

For illustrative purposes, the present invention will be described in the context of a cardiac diagnostic or therapeutic procedure, such as an electrophysiology study. One of ordinary skill in the art will appreciate, however, that the invention may be practiced with equal success in any number of other applications, and, accordingly, the illustrative embodiment used herein to describe the invention should not be regarded as limiting.

Figure 1:
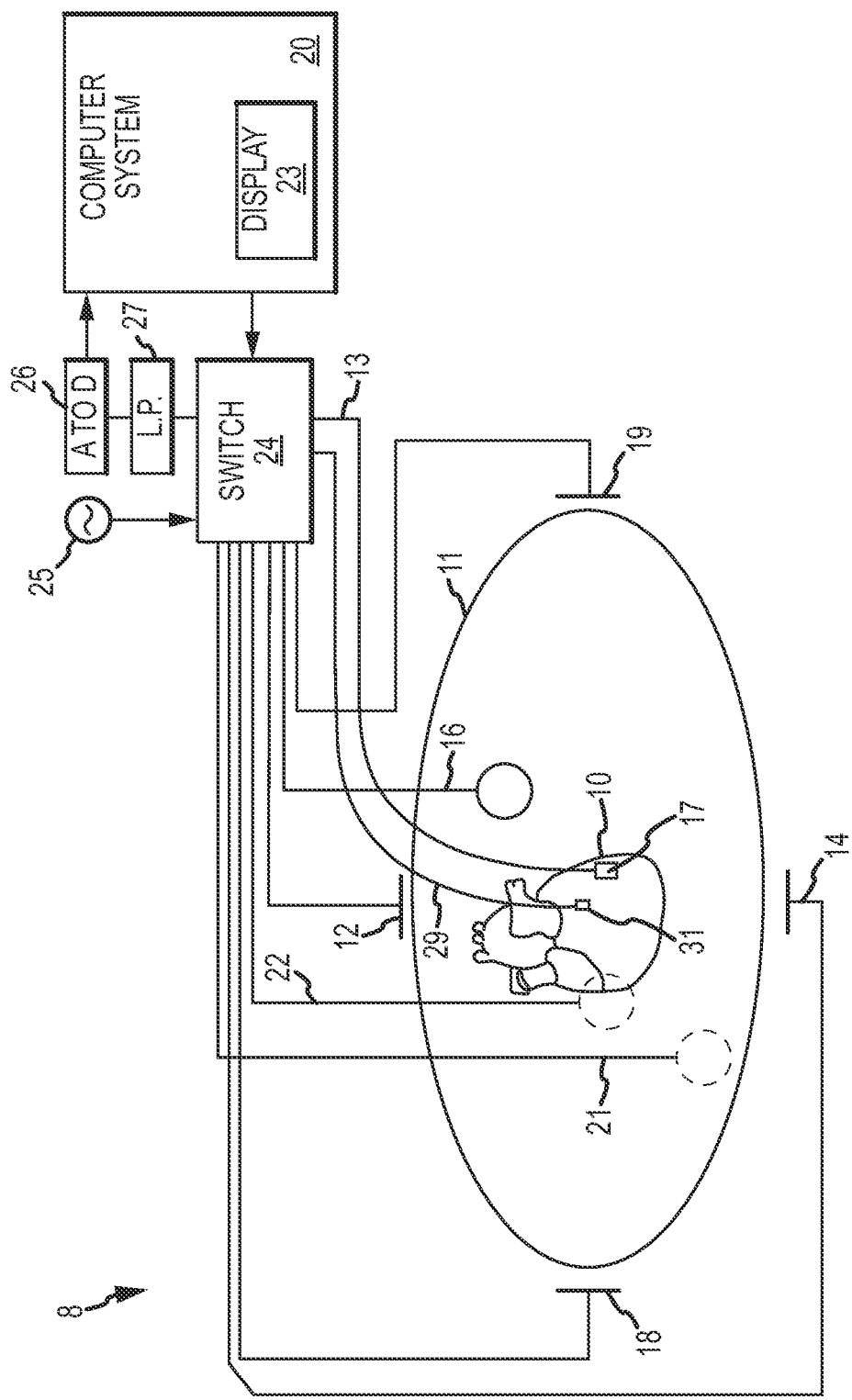
FIG. 1 is a schematic depiction of a localization system such as may be utilized in an electrophysiology study.

FIG. 1 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. As discussed in greater detail below, localization system 8 is preferably a non-ionizing localization system, such as a localization system that generates electrical and/or magnetic fields.

System 8 can be used, for example, to create an anatomical model of the patient's heart 10 using one or more electrodes (or other suitable localization elements). As one of ordinary skill in the art will recognize, and as will be further described below, localization system 8 determines the location (and, in some aspects, the orientation) of objects, typically within a three-dimensional space, and expresses those locations as position information determined relative to at least one reference. System 8 can also be used to measure electrophysiology data at a plurality of points along a cardiac surface, and to store the measured data in association with location information for each measurement point at which the electrophysiology data was measured, for example to create a diagnostic data map of the patient's heart 10.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. Likewise, the electrodes do not need to be on the body surface, but could be fixed on an external apparatus, or electrodes positioned internally to the body could be used.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode 21 (e.g., a "belly patch") provides a reference and/or ground electrode for the system 8. The belly patch electrode 21 may be an alternative to a fixed intracardiac electrode 31, described in further detail below. It should also be appreciated that, in addition, the patient 11 may have most or all of the conventional electrocardiogram ("ECG" or "EKG") system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," "measurement electrode," or "position measurement sensor" throughout this specification. Electrode 17 is also a "localization element," as that term is defined below. Typically, multiple electrodes on catheter 13, and/or on multiple such catheters, will be used. In one embodiment, for example, localization system 8 may comprise sixty-four electrodes on twelve catheters disposed within the heart and/or vasculature of the patient. Of course, this embodiment is merely exemplary, and any number of electrodes and catheters may be used within the scope of the present invention.

Figure 2:
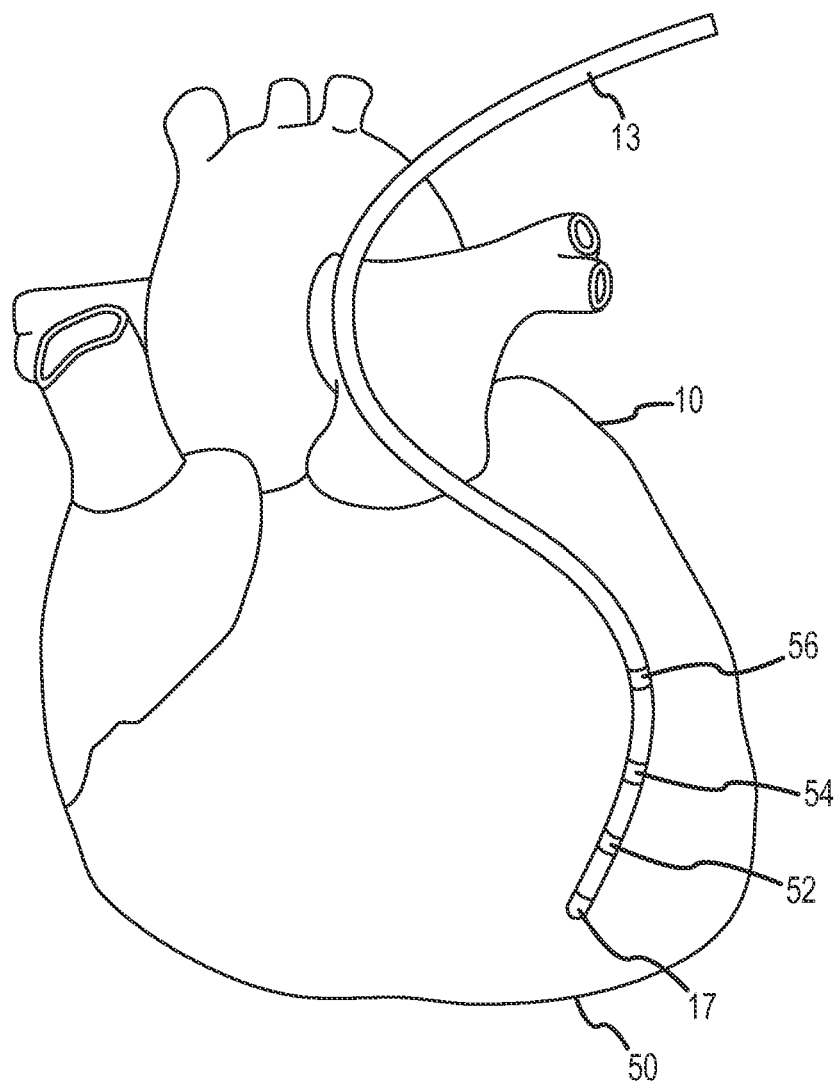
FIG. 2 is a representative catheter that may be used in connection with the localization system depicted in FIG. 1.

For purposes of this disclosure, an exemplary catheter 13 is shown in FIG. 2. In FIG. 2, catheter 13 extends into the left ventricle 50 of the patient's heart 10. Catheter 13 includes electrode 17 on its distal tip, as well as a plurality of additional measurement electrodes 52, 54, 56 spaced along its length. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by localization system 8. Thus, each electrode (e.g., 17, 52, 54, 56) may generate a localization signal that describes the position, and optionally also the orientation, of catheter 13 within the localization field generated by patch electrodes 12/14, 18/19, and 16/22.

Returning now to FIG. 1, an optional fixed reference electrode 31 (e.g., attached to a wall of the heart 10 or anchored within the coronary sinus) is shown carried on a second catheter 29. For calibration purposes, electrode 31 may be stationary (e.g., attached to or near the wall of the heart) or disposed in a fixed spatial relationship with the roving electrodes (e.g., electrodes 17, 52, 54, 56), and thus constitutes a "navigational reference" as that term is defined above. Electrode 31 may also be referred to as a "local reference." Likewise, catheter 29, which carries electrode 31, constitutes a "reference catheter" as that term is defined above.

The fixed reference electrode 31 may be used in addition to or as an alternative to the surface reference electrode 21 described above. In many instances, a coronary sinus electrode or other fixed electrode in the heart 10 can be used as a reference for measuring voltages and displacements; that is, as described herein, fixed reference electrode 31 may define the origin of a coordinate system for the localization field. It should also be understood that reference catheter 29 typically carries multiple electrodes, for example as shown in FIG. 2, and that a user of localization system 8 may designate one such electrode (e.g., reference electrode 31) as the navigational reference for a particular procedure.

Each surface electrode is coupled to the multiplex switch 24, and pairs of surface electrodes are selected by software running on a computer 20, which couples the surface electrodes to a signal generator 25. The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The measurement electrodes (e.g., roving electrodes 17, 52, 54, 56) placed in the heart 10 are exposed to the field from a current pulse and are measured with respect to ground, such as belly patch 21. In practice, the catheters within the heart may contain more or fewer electrodes than the four shown, and each electrode potential may be measured. As previously noted, at least one electrode (e.g., reference electrode 31) may be fixed to the interior surface of the heart to form a fixed navigational reference, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. For purposes of this disclosure, the invention will be described in connection with a three-dimensional (x, y, z) Cartesian coordinate system. It should be understood, however, that other coordinate systems, such as spherical and cylindrical coordinate systems in three dimensions and polar coordinate systems in two dimensions, are within the scope of the invention.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described in co-pending U.S. application Ser. No. 11/227,580, filed 15 Sep. 2005, which is also incorporated herein by reference in its entirety.

In summary, the system 8 first selects a set of surface electrodes and then drives them with current pulses. While the current pulses are being delivered, electrical activity, such as the voltages measured at at least one of the remaining surface electrodes and in vivo electrodes, is measured and stored. Compensation for artifacts, such as respiration and/or impedance shifting, may be performed as indicated above.

In a preferred embodiment, the localization system is the EnSite NavX™ navigation and visualization system of St. Jude Medical, Atrial Fibrillation Division, Inc., which generates electrical fields as described above. Other localization systems, however, may be used in connection with the present invention, including for example, the CARTO navigation and location system of Biosense Webster, Inc., or the AURORA® system of Northern Digital Inc., both of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The field generated by localization system 8, whether an electrical field (e.g., EnSite NavX™), a magnetic field (e.g., CARTO, AURORA®), or another suitable field, may be referred to generically as a "localization field," while the elements generating the fields, such as surface electrodes 12, 14, 16, 18, 19, and 22 may be generically referred to as "localization field generators." Likewise, though the present invention is described primarily in the context of a localization system that generates an electrical field, such that catheters 13 and 29 carry electrodes, one of ordinary skill in the art will understand how to apply the principles disclosed herein in other types of localization fields, and in particular other types of non-ionizing localization fields (e.g., by replacing electrodes 17, 52, 54, 56 with coils to detect different components of a magnetic field). Thus, the term "localization element" is used herein to refer generically to an element whose position within the localization field generated by system 8 can be measured.

As one of ordinary skill in the art will recognize, and as described above, reference electrode 31 may become dislodged from its initial reference location during the course of an electrophysiology study, for example if the physician inadvertently tugs on reference catheter 29, effectively moving the origin of the coordinate system relative to which the positions of the roving electrodes (e.g., 17, 52, 54, and 56) are measured and invalidating any such measurements made after the dislodgement. It is desirable, therefore, for a controller (e.g., a processor, such as that incorporated into computer system 20) to monitor for dislodgement of the navigational reference from the initial reference location, and, if such dislodgement occurs, to generate a signal indicative of the dislodgement, for example to alert the user that a dislodgement has occurred, thereby enabling the user to take corrective action.

One challenge in detecting dislodgements of the navigational reference is that the navigational reference is located within a patient and is constantly moving due to, for example, the patient's cardiac and respiratory activity. Moreover, various electrical and pharmacological interferences could make it appear that the navigational reference has dislodged when, in fact, it has not. Thus, it is desirable to distinguish such "false" or "perceived" dislodgements of reference catheter 29 due to these external influences from actual mechanical dislodgements of reference catheter 29.

The present invention leverages the phenomenon that the most likely mechanical dislodgements of reference catheter 29, when it is placed into a blood vessel (e.g., the coronary sinus), are along the catheter axis or deviate only relatively slightly therefrom (that is, they are in a predictable or anticipated dislodgement direction). The present invention, therefore, correlates the displacement of the reference localization elements (e.g., electrodes) on reference catheter 29 with the anticipated dislodgement direction (e.g., the direction of the axis of reference catheter 29), and reports dislodgement if this correlation is high (e.g., if the displacement is significant and largely parallel to or nearly parallel to the catheter axis).

Figure 3:
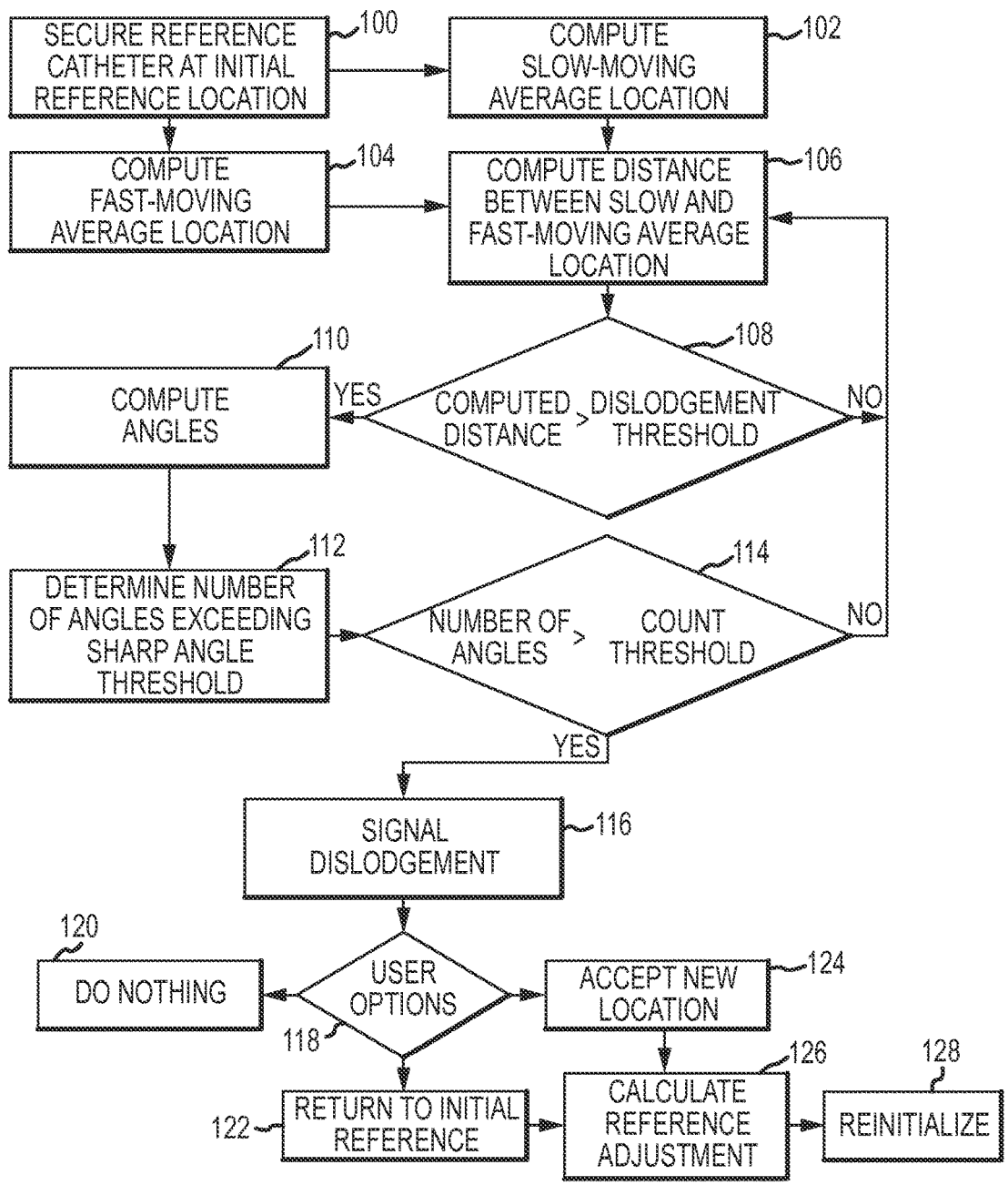
FIG. 3 is a flowchart that illustrates navigational reference dislodgement detection and mitigation functions according to an embodiment of the present invention.

Various aspects of the inventive method of detecting dislodgement of a navigational reference will now be described with reference to FIG. 3. In block 100, a reference catheter (e.g., reference catheter 29) including a plurality of reference electrodes (or other suitable localization elements) is secured at an initial reference location within the localization field. For example, reference catheter 29 may be inserted into a patient's coronary sinus, and reference electrode 31 thereon may be designated as the navigational reference (i.e., the origin of the coordinate system for localization system 8).

In block 102, the slow-moving average location of one or more of the reference electrodes on reference catheter 29 is computed. For purposes of illustration, this disclosure describes an embodiment of the invention where all of the reference electrodes on reference catheter 29 are employed. It should be understood, however, that fewer than all reference electrodes can be employed within the spirit and scope of the present invention, and one of ordinary skill in the art will appreciate how to adapt the present teachings accordingly.

Thus, for purposes of the embodiment of the invention described herein, the (x, y, z) coordinates of all of the reference electrodes on reference catheter 29 are measured and filtered with a moving average filter having a filter time constant of several minutes. In effect, the slow-moving average location "smooths" the effects of patient cardiac and respiratory activity, as well as the effects of certain electrical and pharmacological interferences, so as to provide a longer term representation of the stable location of the reference electrodes. Of course, other methodologies of computing the stable location of the reference electrodes may also be employed without departing from the spirit and scope of the present invention.

Simultaneously, in block 104, the fast-moving average location of the reference electrodes on reference catheter 29 is computed. In some embodiments of the invention, the fast-moving average location is computed by measuring the (x, y, z) coordinates of all of the reference electrodes on reference catheter 29 and filtering these measurements with a moving average filter, preferably having a time constant of about 12 seconds. Of course, the moving average filter may also have a varying or adaptively varying time constant.

Suitable filter implementations for the computation of the slow- and fast-moving average locations of the reference electrodes include, without limitation, exponential moving average filters, moving average filters, infinite impulse response filters, finite impulse response filters, and any combinations thereof.

As one of ordinary skill in the art will appreciate, the fast-moving average location provides a more "instantaneous" picture of the position of reference catheter 29 by removing cardiac and respiratory artifacts from the localization signals of the various reference electrodes. There are, however, alternatives to the moving average filter described above that may be employed without departing from the scope of the invention. For example, in some embodiments of the invention, the respiration compensation methodology disclosed in U.S. Pat. No. 7,263,397 may be employed to remove respiratory artifacts from the localization signal. The respiration filtering methodology disclosed in U.S. application Ser. No. 12/835,518, filed 13 Jul. 2010 and hereby incorporated by reference as though fully set forth herein, may also be employed to good advantage in connection with the present invention.

In block 106, distances between the slow- and fast-moving average locations of the reference electrodes on reference catheter 29 are computed. This distance generally reflects how far away from the initial reference position reference catheter 29 is (or appears to be) at any given moment in time.

In decision block 108, as a first-order detection of a potential mechanical dislodgement of reference catheter 29, a comparison is made between the distance computed in block 106 and a preset dislodgement threshold. The preset dislodgement threshold is chosen to reflect a distance below which a mechanical dislodgement of reference catheter 29 is unlikely and/or clinically insignificant, and will typically be about 4 mm. If the distance computed in block 106 does not exceed the dislodgement threshold (e.g., it is less than about 4 mm), then it is unlikely that reference catheter 29 has dislodged from the initial reference location and/or any such dislodgement is clinically insignificant, and the analysis returns to block 106. If, on the other hand, the distance computed in block 106 exceeds the dislodgement threshold (e.g., it is greater than about 4 mm), further analysis can be conducted to determine whether reference catheter 29 has, in fact, dislodged from the initial reference location, or whether there has merely been a perceived dislodgement (due, for example, to patient respiration).

This second-order analysis examines whether the perceived displacement of reference catheter 29 occurred in the direction along which mechanical dislodgements are anticipated (e.g., along the axis of the catheter). Thus, in some embodiments of the invention, in block 110, a series of angles are computed. First, for each of the reference electrodes on reference catheter 29, a vector connecting the slow- and fast-moving average locations thereof when the distance exceeded the dislodgement threshold (e.g., at the time of the potential dislodgement) is computed. Then, the angle between this vector and the axis of reference catheter 29 proximate the reference electrode (which may be referred to as the "local axis" of reference catheter 29) is computed, which correlates the direction of movement of reference catheter 29 with the direction of the local axis thereof. As described above, a high correlation between the direction of movement of reference catheter 29 and the local axis of reference catheter 29 suggests a mechanical dislodgement as opposed to a "false" dislodgement. Thus, each reference electrode on reference catheter 29 will have an associated angle.

The local axis of reference catheter 29 may be determined in a number of ways. For example, the local axis may be determined by computing a line segment connecting each reference electrode to a neighboring reference electrode or from the known geometry of reference catheter 29. In other embodiments, the local axis of reference catheter 29 may be computed by computing a line segment connecting neighboring reference electrodes. In still other embodiments of the invention, the local axis of reference catheter 29 may be computed as a tangent to the body of reference catheter 29.

In block 112, the angles computed in block 110 are analyzed to determine how many such angles exceed a preset sharp angle threshold. This step measures the correlation between the displacement of the reference electrodes and the catheter axis; as discussed above, the most likely mechanical dislodgements of reference catheter 29 are along or relatively close to the axis thereof. The sharp angle threshold, therefore, is preferably near 0 degrees or near 180 degrees, depending on the convention adopted to define the local axis of reference catheter 29.

In decision block 114, the number of angles exceeding the sharp angle threshold is compared to a preset count threshold. The count threshold is selected to reflect the number of reference electrodes that must experience a displacement along or nearly along the axis of the catheter to support a conclusion that reference catheter 29 has dislodged from the initial reference location. That is, if a high number of reference electrodes experienced a displacement along or nearly along the axis of the catheter, it is likely that reference catheter 29 has dislodged from the initial reference location. If, on the other hand, a low number of reference electrodes experienced a displacement along or nearly along the axis of the catheter, then it is unlikely that reference catheter 29 has dislodged from the initial reference location.

Thus, if the number of angles exceeding the sharp angle threshold falls below the count threshold (that is, if relatively fewer of the reference electrodes experienced a displacement along or nearly along the axis of reference catheter 29), then the system concludes that there has not been a dislodgement of reference catheter 29 and the analysis returns to block 106. If, on the other hand, the number of angles exceeding the sharp angle threshold exceeds the count threshold (that is, if relatively more of the reference electrodes experienced a displacement along or nearly along the axis of reference catheter 29), then the system concludes that there has been a dislodgement of reference catheter 29 and a suitable signal (e.g., an audible signal, a visible signal, or a combination thereof) is generated in block 116.

Once dislodgement has been detected, the practitioner is offered three options in decision block 118. First, the user may opt to do nothing (block 120).

Second, the user may choose to return reference catheter 29 to the initial reference location (or, more likely, a location reasonably proximate thereto) (block 122). If the user elects this option, then, as discussed in further detail below, visual and/or audible guidance may be provided to aid the user in doing so. For example, the system may show an image of the current location of reference catheter 29 as well as a "shadow" image of reference catheter 29 in the initial reference location. Alternatively, the system may show an image of the current location of reference catheter 29 and a target to which the user is attempting to move reference catheter 29.

The system may also provide audible guidance to indicate the proximity of reference catheter 29 to the initial reference location, such as a beeping tone that increases in frequency as reference catheter 29 approaches the initial reference location.

It is also contemplated that the system may provide positional guidance to an automated catheter control system, such as the robotic surgical system disclosed in U.S. application Ser. No. 11/647,298, filed 29 Dec. 2006, which is hereby incorporated by reference as though fully set forth herein.

Third, the user may choose to accept the new, displaced location of reference catheter 29 as a new reference location (block 124). If the user elects this option, then a reference adjustment is preferably calculated in block 126 to compensate for any change in position of reference catheter 29 after its dislodgement from the initial reference location. This reference adjustment is, in effect, a transformation function or vector that transforms coordinates measured relative to the new location of navigational reference 31 to the coordinate system prior to the dislodgement of reference catheter 29, and thus is used to adjust position measurements made by localization system 8 after the dislodgement.

Of course, it may also be desirable to calculate a reference adjustment when the user elects to reposition reference catheter 29 in the initial reference location, insofar as it is unlikely that the user will be able to return reference catheter 29 to the same exact location as it occupied prior to the dislodgement.

Finally, if the user elects to mitigate the dislodgement (that is, the user opts to do anything other than nothing in response to the dislodgement), the dislodgement detection process may be re-initialized in block 128. During the re-initialization process, dislodgement monitoring is temporarily suspended. When dislodgement monitoring is suspended, the locations of the slow-moving averages of all reference electrodes on reference catheter 29 immediately prior to the dislodgement are stored (so that they may be used, for example, to calculate a reference adjustment as described above) and the new stable locations of the reference electrodes on reference catheter 29 are averaged over a waiting period to set a new slow-moving average location baseline for the dislodgement detection method described herein. At the conclusion of the waiting period (i.e., once a new slow-moving average baseline is established), dislodgement monitoring is re-enabled.

It is also contemplated that the present invention may be practiced in connection with integrated electric- and magnetic-field based localization systems, such as the gMPS™ Medical Positioning System. For example, in addition to measuring the location of reference electrodes on reference catheter 29 using an electric-field based localization system, the location of an electro-magnetic reference localization element (e.g., an electro-magnetic transducer) may be measured using a magnetic-field based localization system.

Likewise, the electro-magnetic reference localization element will have an axis that can be measured by the magnetic-field based localization system; it should be appreciated that the axis of this element will be nearly parallel to the local axis of reference catheter 29.

With respect to the electro-magnetic reference localization element, both a dislodgement vector (that is, a vector connecting the slow- and fast-moving average locations of the electro-magnetic reference localization element) and a dislodgement angle (that is, the angle between the dislodgement vector and the local axis of reference catheter 29) may be computed. If the dislodgement angle is below a preset threshold (similar in nature to the sharp angle threshold described above), then it is further evidence that reference catheter 29 has dislodged from the initial reference location.

Figure 4:
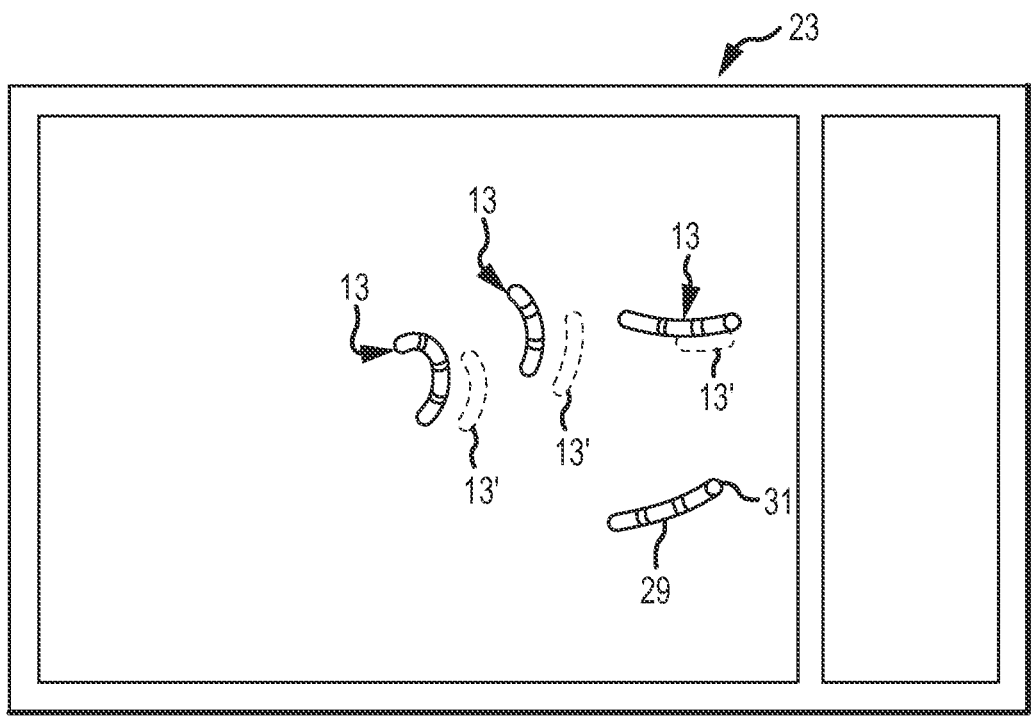
FIGS. 4 through 7 illustrate an application of a method of detecting and mitigating navigational reference dislodgement according to an embodiment of the present invention.

An application of the present inventive method will now be described with reference to FIGS. 4 through 7. FIG. 4 represents the initial state of the system with dislodgement detection enabled. Reference catheter 29 is visible, as is reference electrode 31 thereon, which has been designated as the navigational reference. Also shown are a series of other catheters 13 carrying measurement electrodes. For purposes of illustration, the actual locations of catheters 13 are shown in phantom as shadows 13'.

Figure 5:
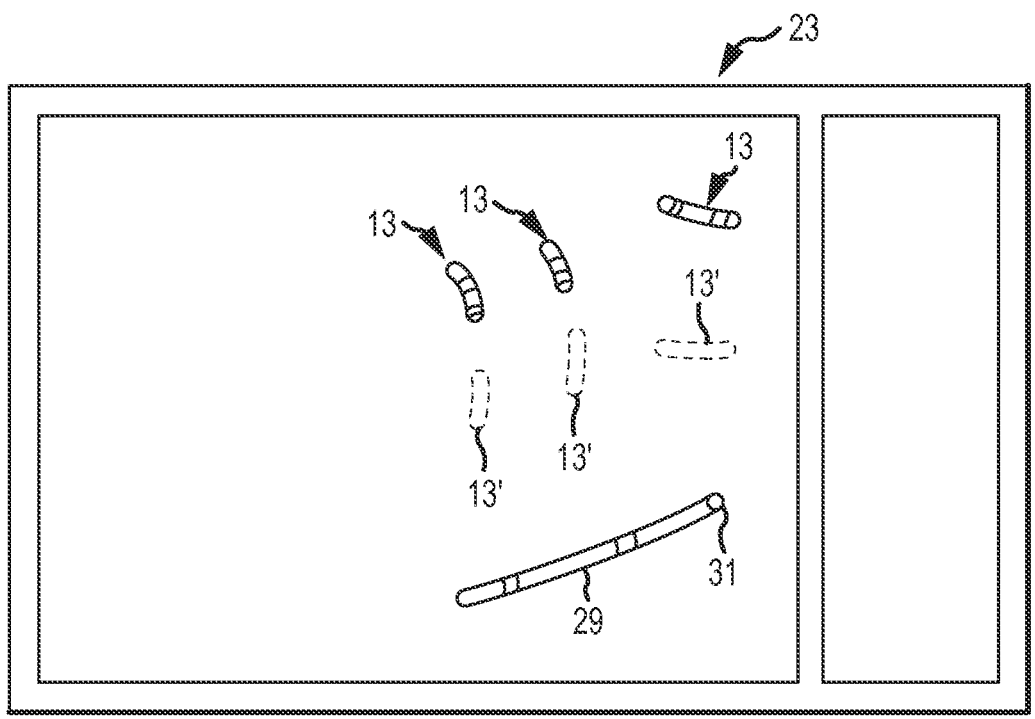

In FIG. 5, reference catheter 29 has been dislodged. Because the navigational reference is presumed stable, reference electrode 31 does not appear to have moved, such that the dislodgement causes reference catheter 29 to appear dilated. Moreover, the dislodgement of reference catheter 29 also causes catheters 13 to appear significantly displaced from their actual positions as indicated by shadows 13'.

Figure 6:
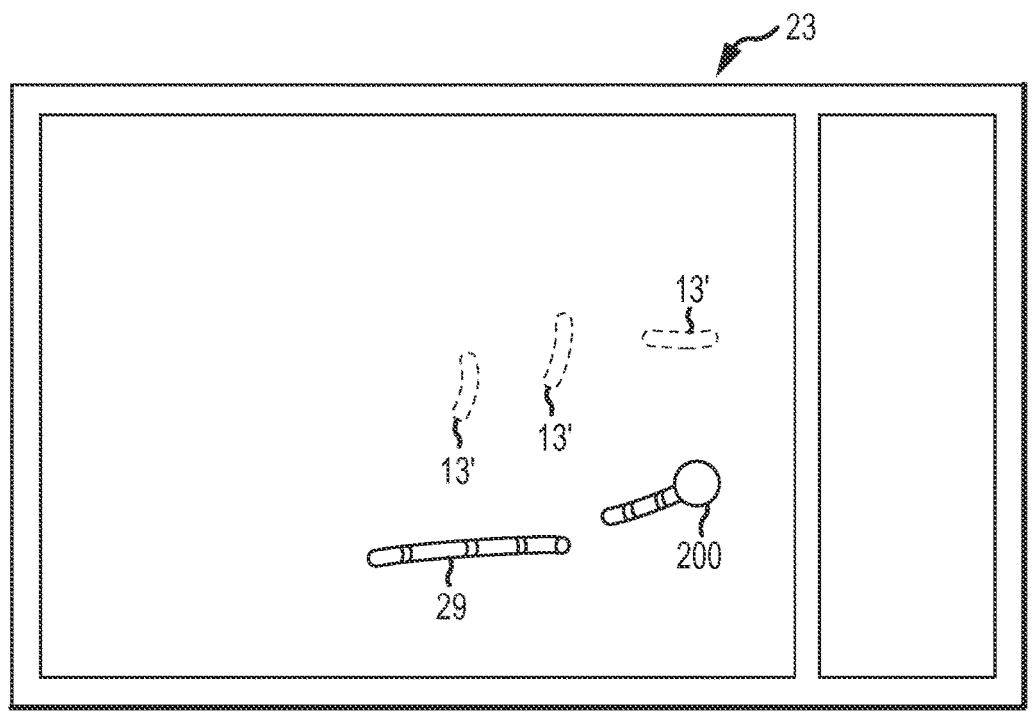

The user may then be alerted to the dislodgement and offered the choice to do nothing or to mitigate the dislodgement, either by repositioning reference catheter 29 proximate the initial reference location or by accepting the displaced location of reference catheter 29 as a new reference location. FIG. 6 assumes that the user has elected to mitigate the dislodgement by repositioning reference catheter 29 proximate the initial reference location.

To aid the user in repositioning reference catheter 29 at or near its initial reference location, the initial reference location (e.g., the original location of reference electrode 31) has been highlighted with a target ball 200. Catheters 13 have also been omitted from FIG. 6 for clarity. As the user moves reference catheter 29, its progress will be reflected on display 23, and visual and/or audible feedback may be provided to the user. For example, as the user moves reference catheter 29 closer to the initial reference location, target ball 200 may change colors (e.g., red when reference catheter 29 is not near the initial reference location, yellow as reference catheter 29 nears the initial reference location, and green when reference catheter 29 coincides with the initial reference location), blink, or otherwise indicate the proximity of reference catheter 29 to the initial reference location.

Figure 7:
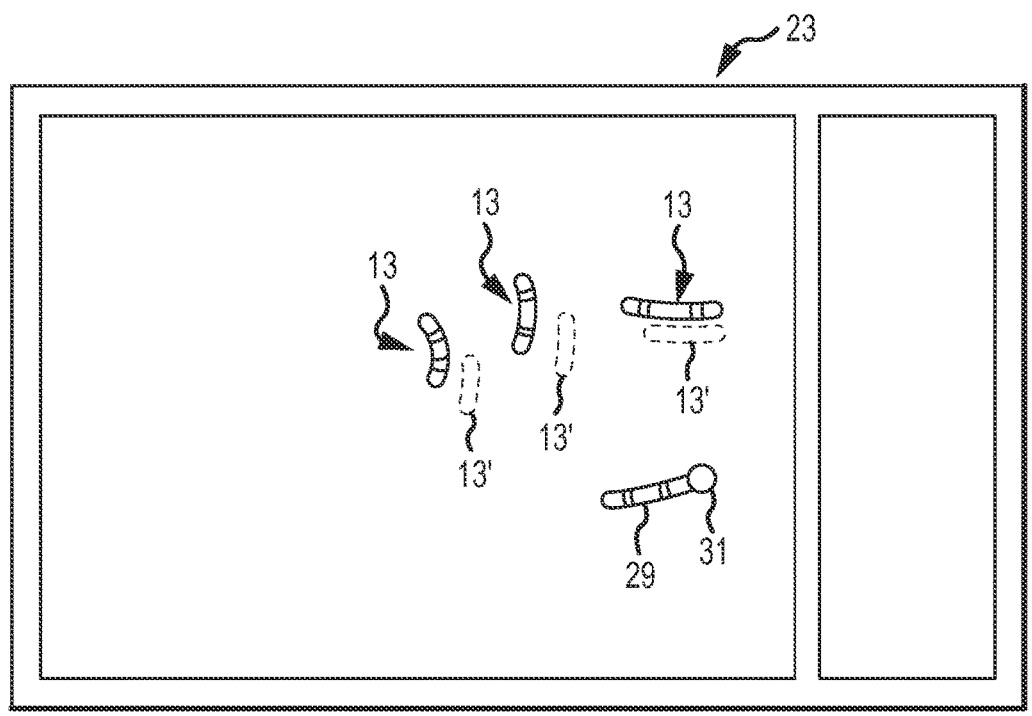

Once the user has returned reference catheter 29 to proximate the initial reference location, the user can accept the new position of reference catheter 29 as a stable reference position. The system will then re-compute the locations of catheters 13, such that they are once again proximate their actual location shadows 13' as shown in FIG. 7. Of course, to the extent that reference catheter 29 is not restored to precisely the same location as its initial reference location, a reference adjustment may be desirable. In addition, the system will re-initialize the dislodgement detection process.

Although several embodiments of this invention have been described above with a certain degree of particularity, those skilled in the art could make numerous alterations to the disclosed embodiments without departing from the spirit or scope of this invention. For example, although the reference adjustment is described as a transformation from the new coordinate system to the old coordinate system, one of ordinary skill in the art will appreciate that transformations could just as well be made from the old coordinate system to the new coordinate system. That is, the reference adjustment is used to ensure that all measurements are made to a common coordinate system; whether that coordinate system is the old system or the new system is not critical.

As another example, one of ordinary skill in the art will appreciate that the embodiments of the invention described herein (e.g., electric-field based localization system, magnetic-field based localization system, and hybrid electric- and magnetic-field based localization systems) may be utilized in any desirable combination (e.g., detecting a dislodgement only if both the reference electrodes and a reference electro-magnetic localization element both exceed a dislodgement threshold and exhibit a displacement in a likely dislodgement direction).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of detecting dislodgement of a navigational reference within a localization field, the method comprising:
   placing a reference catheter including at least one reference localization element within a localization field;
   securing the reference catheter at an initial reference location within the localization field;
   computing a slow-moving average location of the at least one reference localization element;
   computing a fast-moving average location of the at least one reference localization element;
   computing a distance between the slow- and fast-moving average locations of the at least one reference localization element;
   comparing the computed distance to a dislodgement threshold; and
   determining that a dislodgement of the reference catheter from the initial reference location has occurred; and
   generating a signal indicative of the dislodgement of the reference catheter from the initial reference location.

2. The method according to claim 1, wherein the dislodgement threshold is about 4 mm.

3. The method according to claim 1, further comprising, if the computed distance exceeds the dislodgement threshold:
   for the at least one reference localization element:
      computing a vector connecting the slow- and fast-moving average locations of the respective reference localization element at a point in time when the computed distance between the slow- and fast-moving average locations of the respective reference localization element exceeded the dislodgement threshold;
      determining an axis of the reference catheter proximate the respective reference localization element at the point in time when the computed distance between the slow- and fast-moving average locations of the respective reference localization element exceeded the dislodgement threshold; and
      computing an angle between the computed vector and the axis of the reference catheter proximate the respective reference localization element,
   thereby computing at least one angle associated with the at least one reference localization element; and
   analyzing the at least one angle for an indication that the reference catheter has dislodged from the initial reference location.

4. The method according to claim 3, wherein the step of analyzing the at least one angle for an indication that the reference catheter has dislodged from the initial reference location comprises:
   determining a count of angles exceeding a sharp angle threshold; and
   comparing the count of angles to a count threshold.

5. The method according to claim 3, wherein the axis of the reference catheter proximate the respective reference localization element is defined by a line segment connecting the respective reference localization element to a neighboring reference localization element.

6. The method according to claim 1, wherein the fast-moving average location of the at least one reference localization element is computed with a filter time constant of about 12 seconds.

7. The method according to claim 1, wherein at least one of the slow- and fast-moving average locations of the at least one reference localization element is computed using a filter selected from the group consisting of: exponential moving average filters, moving average filters, infinite impulse response filters, finite impulse response filters, and any combinations thereof.

8. The method according to claim 1, further comprising providing guidance to a user to help re-position and secure the reference catheter proximate the initial reference location.

9. The method according to claim 1, further comprising:
defining a new stable location of the reference catheter;
calculating a reference adjustment to compensate for any change in position of the reference catheter between the initial reference location and the new stable location; and
using the reference adjustment to adjust localization element position measurements made after the dislodgement from the initial reference location.

10. A method of detecting dislodgement of a navigational reference within a non-ionizing localization field, the method comprising:
securing a reference catheter including a plurality of reference localization elements at an initial reference location within the localization field;
detecting a perceived displacement of the reference catheter from the initial reference location;
analyzing a direction of the perceived displacement to determine whether there has been a dislodgement of the reference catheter from the initial reference location; and
generating a signal indicating the dislodgement of the reference catheter from the initial reference location.

11. The method according to claim 10, further comprising:
calculating a reference adjustment to compensate for any change in position of the reference catheter after the dislodgement from the initial reference location; and
using the reference adjustment to adjust localization element position measurements made after the dislodgement from the initial reference location.

12. The method according to claim 10, wherein the detecting step comprises comparing a magnitude of a perceived displacement of at least some of the plurality of reference localization elements to a dislodgement threshold.

13. The method according to claim 10, wherein the analyzing step comprises comparing a direction of a perceived displacement of at least some of the plurality of reference localization elements to an anticipated dislodgement direction.

14. The method according to claim 10, further comprising providing guidance to a user to help re-position and secure the reference catheter proximate the initial reference location.

15. A localization system, comprising:
a plurality of localization field generators;
a reference catheter including a plurality of reference localization elements; and
a reference catheter dislodgement processor that monitors for a dislodgement of the reference catheter from an initial reference location based, at least in part, on a difference between a slow-moving average location and a fast-moving average location of at least one of the plurality of reference localization elements on the reference catheter.

16. The localization system according to claim 15, wherein the reference catheter dislodgement processor:
compares the difference between the slow-moving average location and the fast-moving average location of at least some of the plurality of reference localization elements to a dislodgement threshold, and, if the difference exceeds the dislodgement threshold:
computes, for at least some of the plurality of reference localization elements, an angle between a vector connecting the slow- and fast-moving average locations of the reference localization element and an axis of the reference catheter proximate the reference localization element, thereby computing a plurality of angles;
determines a count of angles exceeding a sharp angle threshold; and
compares the count of angles to a count threshold to determine whether the reference catheter has dislodged from the initial reference location.

17. The localization system according to claim 15, further comprising a reference adjustment processor that:
calculates a reference adjustment to compensate for any change in position of the reference catheter after the dislodgement from the initial reference location; and
uses the reference adjustment to adjust localization element position measurements made after the dislodgement from the initial reference location.

18. The localization system according to claim 15, wherein the reference catheter dislodgement processor monitors for a dislodgement of the reference catheter from an initial reference location based, at least in part, on a correlation between a direction of perceived dislodgement of the reference catheter and a direction of anticipated dislodgement of the reference catheter.

* * * * *